US009267788B2

(12) United States Patent
Yamamoto et al.

(10) Patent No.: US 9,267,788 B2
(45) Date of Patent: Feb. 23, 2016

(54) OPTICAL SENSOR HAVING LIGHT GUIDE MEMBERS WITH CHARACTERISTIC DETECTION PORTIONS WHOSE OPTICAL CHARATERISTICS VARY IN ACCORDANCE WITH A PHYSICOCHEMICAL STATE

(71) Applicant: OLYMPUS CORPORATION, Tokyo (JP)

(72) Inventors: Eiji Yamamoto, Musashimurayama (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 136 days.

(21) Appl. No.: 14/277,423

(22) Filed: May 14, 2014

(65) Prior Publication Data

US 2014/0246572 A1 Sep. 4, 2014

Related U.S. Application Data

(63) Continuation of application No. PCT/JP2012/079375, filed on Nov. 13, 2012.

(30) Foreign Application Priority Data

Nov. 15, 2011 (JP) .................................. 2011-249656

(51) Int. Cl.
*G01D 5/353* (2006.01)
*G01B 11/24* (2006.01)
(Continued)

(52) U.S. Cl.
CPC ............ *G01B 11/24* (2013.01); *A61B 1/00167* (2013.01); *G01B 11/16* (2013.01); *G01D 5/35345* (2013.01)

(58) Field of Classification Search
CPC ...... G01D 5/353; G01D 5/268; G01D 5/3537; G01N 21/94; G01N 21/783
USPC .............. 250/227.11, 227.14, 227.16, 227.18, 250/222.2, 221, 214.1; 385/11–13; 356/432–440
See application file for complete search history.

(56) References Cited

U.S. PATENT DOCUMENTS 4,285,570 A 8/1981 Minemura et al.
4,827,121 A * 5/1989 Vidrine, Jr. .......... G01N 21/552
250/227.23

FOREIGN PATENT DOCUMENTS

JP 53-113002 A 9/1978
JP 55-029481 U1 2/1980
(Continued)

OTHER PUBLICATIONS

International Preliminary Report on Patentability together with the Written Opinion dated Mar. 5, 2013 received in related International Application No. PCT/JP2012/079375.
(Continued)

*Primary Examiner* — Que T Le
(74) *Attorney, Agent, or Firm* — Scully, Scott, Murphy & Presser, PC

(57) ABSTRACT

An optical sensor includes a light source, a light supply light guide member optically coupled to the light source, detection light guide members, a light distribution unit to distribute light from the light supply light guide member to the detection light guide members, and a light separating detector to separate and detect the light guided by the detection light guide members. Each of the detection light guide members includes a characteristic detection portion whose optical characteristics vary in accordance with a physicochemical state.

24 Claims, 6 Drawing Sheets

(51) Int. Cl.
*G01B 11/16* (2006.01)
*A61B 1/00* (2006.01)

(56) References Cited

FOREIGN PATENT DOCUMENTS

| JP | 56-043603 A | 4/1981 |
|----|-------------|--------|
| JP | 01-281412 A | 11/1989 |
| JP | 01-291203 A | 11/1989 |
| JP | 04-015543 A | 1/1992 |
| JP | 2002-533708 A | 10/2002 |
| JP | 2003-004972 A | 1/2003 |
| JP | 2007-044412 A | 2/2007 |
| WO | WO 00/39531 A1 | 7/2000 |

OTHER PUBLICATIONS

Danisch, L.A. et al., "Bend-enhanced fiber optic sensors", Fiber Optic and Laser Sensors X, (1992), vol. 1795, pp. 204-214.

Microfilm of the specification and drawings annexed to the request of Japanese Utility Model Application No. 113002/1978 (Laid-open No. 29481/1980), Feb. 26, 1980, p. 7, line 19 to p. 8, line 13; fig. 1, corresponding to U.S. Pat. No. 4,285,570 A.

International Search Report dated Mar. 5, 2013 issued in PCT/JP2012/079375.

Japanese Office Action dated Jun. 16, 2015 from related Japanese Patent Application No. 2011-249656, together with an English language translation.

* cited by examiner

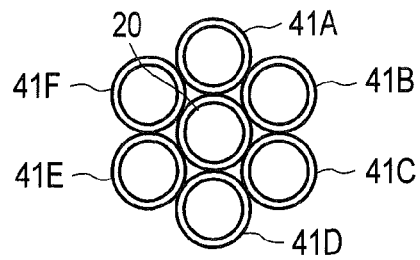
F I G. 7
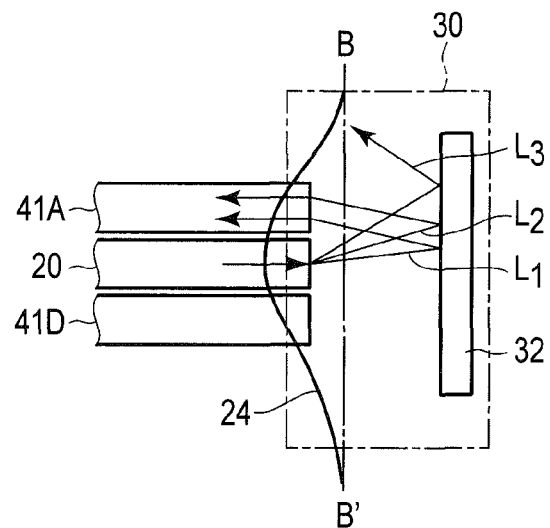
F I G. 8
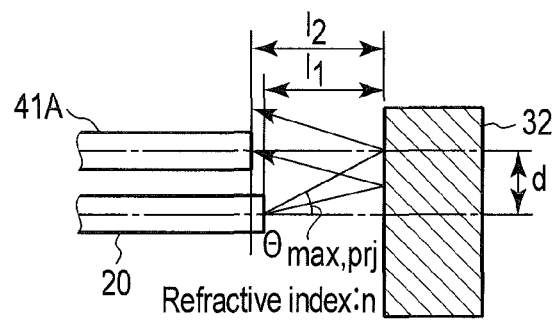
F I G. 9

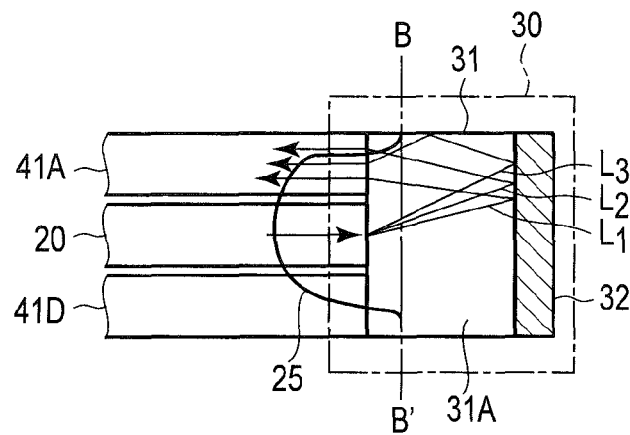
F I G. 10
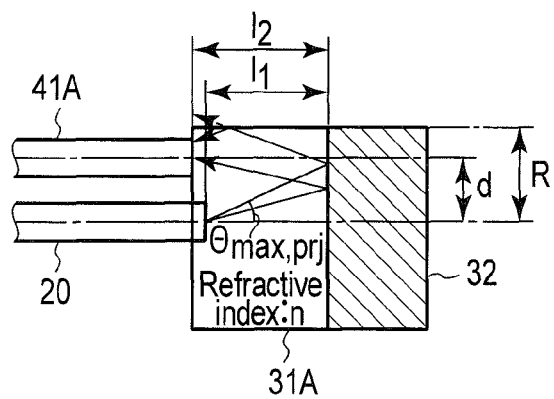
F I G. 11
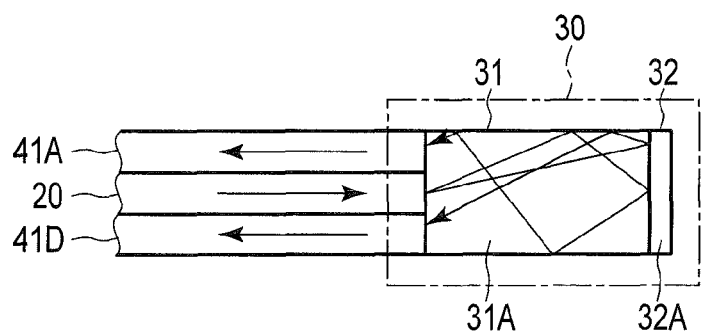
F I G. 12

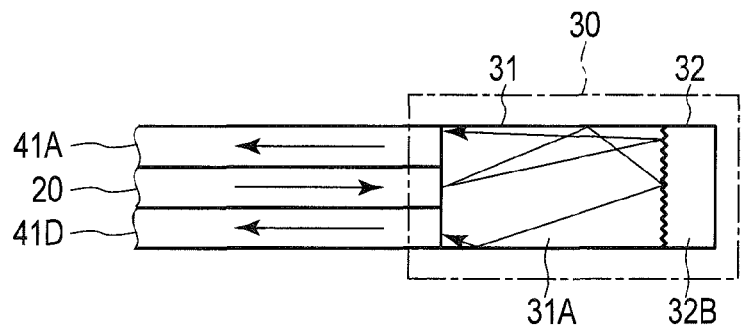
F I G. 13
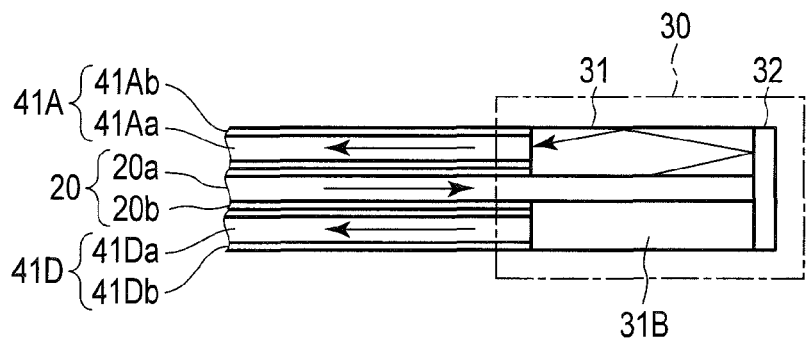
F I G. 14
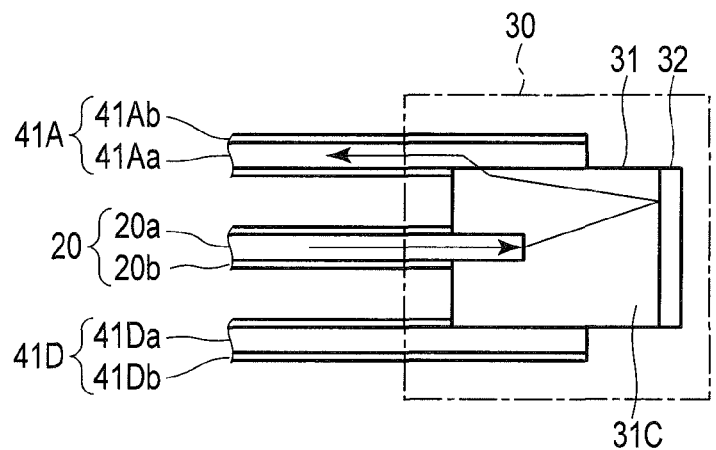
F I G. 15

OPTICAL SENSOR HAVING LIGHT GUIDE MEMBERS WITH CHARACTERISTIC DETECTION PORTIONS WHOSE OPTICAL CHARATERISTICS VARY IN ACCORDANCE WITH A PHYSICOCHEMICAL STATE

CROSS-REFERENCE TO RELATED APPLICATIONS

This application is a Continuation Application of PCT Application No. PCT/JP2012/079375, filed Nov. 13, 2012 and based upon and claiming the benefit of priority from Japanese Patent Application No. 2011-249656, filed Nov. 15, 2011, the entire contents of all of which are incorporated herein by reference.

BACKGROUND OF THE INVENTION

1. Field of the Invention

The present invention relates to an optical sensor using a light guide member.

2. Description of the Related Art

Lee A. Danisch, "Bend-enhanced fiber optic sensor", SPIE vol. 1795 Fiber Optic and Laser Sensors X (1992) pp. 204-214 discloses a curvature sensor using an optical fiber. In this curvature sensor, a curvature detection portion is provided in part of the optical fiber. The optical fiber is constituted of a core and a clad, and the curvature detection portion is formed by damaging part of the clad. In light that is guided through the optical fiber, light that has reached the curvature detection portion is scattered by the curvature detection portion, and part of this light is radiated to the outside of the optical fiber. An amount of this light that is radiated to the outside varies in accordance with an amount and a direction of a curvature of the optical fiber. Therefore, measuring a light guide loss of the optical fiber can obtain an amount of curvature of the optical fiber.

Jpn. Pat. Appln. KOKAI Publication No. 2007-44412 discloses a curvature sensor that can detect curvatures at positions. This curvature sensor includes a light supply fiber and detection fibers. The detection fibers are arranged around the light supply fiber. Both an end of the light supply fiber and an end of each detection fiber are covered with a single mirror, and light exiting the light supply fiber is reflected by the mirror and enters each detection fiber.

Each curvature detection portion is formed in each detection fiber. The two detection fibers form one pair. The curvature detection portions are provided in the detection fibers at positions that are different from each other along a longitudinal direction in accordance with each pair. Although the curvature detection portions of the two detection fibers in the same pair are placed at the same position in the longitudinal direction, their positions around a center axis are different from each other. Therefore, in this curvature sensor, measuring a light guide loss of each detection optical fiber enables obtaining an amount of curvature and a direction of curvature at each of positions.

In the curvature sensor in Jpn. Pat. Appln. KOKAI Publication No. 2007-44412, the light exiting the a light supply fiber must be preferably distributed to the detection fibers, but the preferred distribution of the light is not described in Jpn. Pat. Appln. KOKAI Publication No. 2007-44412 at all. Specifically, this literature just gives a description that the light exiting the light supply fiber is reflected by the mirror and enters the detection fibers. As described above, in the configuration that an end of the light supply fiber and an end of each detection fiber are covered with the single mirror, the preferred distribution of the light cannot be expected.

BRIEF SUMMARY OF THE INVENTION

An optical sensor according to the present invention includes a light source, a light supply light guide member optically coupled to the light source, detection light guide members each of which includes a characteristic detection portion whose optical characteristics vary in accordance with a physicochemical state, a light distribution unit to distribute light from the light supply light guide member to the detection light guide members, and a light separating detector to separate and detect the light guided by the detection light guide members.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 7 shows a positional relationship between a light supply optical fiber and light detection optical fibers shown in FIG. 6 in a cross section vertical to an optical axis;

FIG. 8 schematically shows a structural example of a light distribution conversion unit of a light distribution unit shown in FIG. 6;

FIG. 9 shows the light supply optical fiber and a light detection optical fiber in the light distribution unit shown in FIG. 8;

FIG. 10 schematically shows another structural example of the light distribution conversion unit of the light distribution unit shown in FIG. 6;

FIG. 11 shows a light supply optical fiber, a transparent member, and a light detection optical fiber in the light distribution unit shown in FIG. 10;

FIG. 12 shows a structural example of a light turnback unit shown in FIG. 6;

FIG. 13 shows another structural example of the light turnback unit shown in FIG. 6;

FIG. 14 shows another structural example of the light distribution unit shown in FIG. 6; and FIG. 15 shows still another structural example of the light distribution unit shown in FIG. 6.

DETAILED DESCRIPTION OF THE INVENTION

First Embodiment

Figure 1:
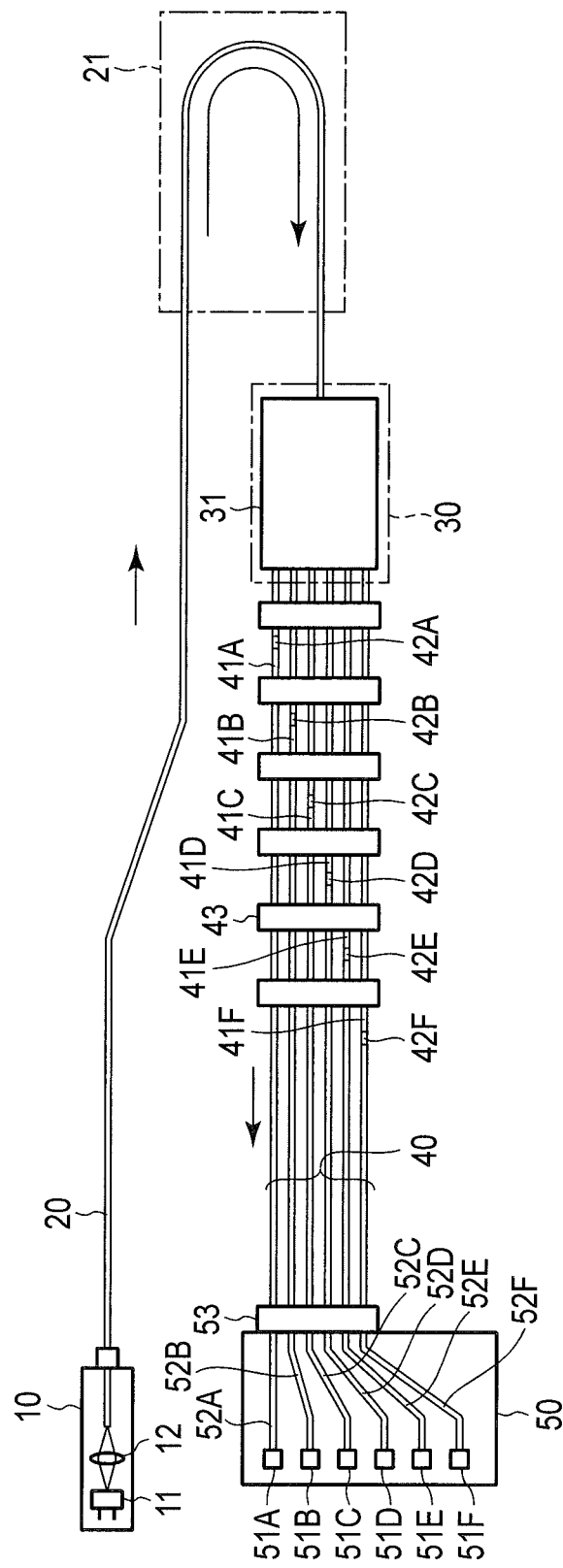
FIG. 1 shows an entire configuration of an optical sensor according to a first embodiment.

A first embodiment according to the present invention will now be described hereinafter in detail with reference to the drawings. It is to be noted that the present invention is not limited by this embodiment. FIG. 1 shows an entire configuration of an optical sensor according to this embodiment.

As shown in FIG. 1, the optical sensor includes a light source 10, an optical fiber 20 optically coupled to the light source 10, an optical fiber bundle 40, a light distribution unit 30 that distributes light from the optical fiber 20 to the optical fiber bundle 40, and a light separating detector 50 that separates and detects light guided through the optical fiber bundle 20.

The light source 10 includes a light emitting element 11 to emit light and a coupling lens 12 to couple the light emitted from the light emitting element 11 to the optical fiber 20.

The optical fiber 20 functions as a light supply light guide member.

The optical fiber bundle 40 includes optical fibers 41A, 41B, 41C, 41D, 41E, and 41F. The optical fibers 41A to 41F have characteristic detection portions 42A, 42B, 42C, 42D, 42E and 42F whose optical characteristics vary in accordance with a physicochemical state, respectively. The optical fibers 41A to 41F function as detection light guide members. The optical fibers 41A to 41F are bundled by tying bands 43 at positions provided at intervals in the longitudinal direction.

The characteristic detection portions 42A to 42F are formed in the optical fibers 41A to 41F on light paths extending from the light distribution unit 30 to the light separating detector 50. The characteristic detection portions 42A to 42F may be formed by damages partially formed on clads of the optical fibers 41A to 41F, for example. The characteristic detection portions 42A to 42F are provided at positions that are different from each other along the longitudinal direction in the optical fibers 41A to 41F, respectively. However, the characteristic detection portions 42A to 42F may include portions provided at the same position along the longitudinal direction in the optical fibers 41A to 41F.

The characteristic detection portions 42A to 42F have, e.g., a curvature detecting function. In this case, the characteristic detection portions 42A to 42F bend in accordance with curvatures of the optical fibers 41A to 41F, respectively, optical characteristics, which are typically a light guide loss vary in dependence upon bent shapes, and characteristics of light, which are typically quantities of light, guided through the optical fibers A to F are changed.

The light separating detector 50 includes optical fibers 52A, 52B, 52C, 52D, 52E, and 52F connected to the optical fibers 41A to 41F through a fiber connector 53, respectively and light receiving elements 51A, 51B, 51O, 51D, 51E, and 51F optically coupled to the optical fibers 52A to 52F, respectively. Each of the light receiving elements 51A to 51F outputs an electrical signal to which a received quantity of light is reflected.

The light distribution unit 30 includes a light distribution conversion unit 31 to convert light distribution characteristics of the light exiting the optical fiber 20 and couple the light to the optical fibers 41A to 41F. The light distribution conversion unit 31 is made of a transparent material having a refractive index of 1 or more. This transparent material functions to suppress spread of the light exiting the optical fiber 20.

The optical fiber 20 is bent 180 degrees at an end loop portion 21. A light exist end face of the optical fiber 20 and light incidence end faces of the optical fibers 41A to 41F are arranged to face each other through the light distribution conversion unit 31. The light exiting the optical fiber 20 is optically coupled to the optical fibers 41A to 41F through the light distribution conversion unit 31.

The light emitted from the light emitting element 11 is converged by the coupling lens 12, enters the optical fiber 20, and is guided through the optical fiber 20. Spread of the light exiting the light exit end face of the optical fiber 20 is suppressed by the light distribution conversion unit 31 and distributed to the optical fibers 41A to 41F. The light distributed to the optical fibers 41A to 41F are guided to the light separating detector 50 through the optical fibers 41A to 41F, respectively. This light separating detector 50 spatially separates and detects the light guided through the optical fibers 41A to 41F by using the light receiving elements 51A to 51F connected to the optical fibers 41A to 41F, respectively.

When the characteristic detection portions 42A to 42F bend due to curvatures of the optical fibers 41A to 41F, optical characteristics vary in dependence upon intensity and a direction of this curvature, and hence optical characteristics of the light output from the optical fibers 41A to 41F change. In this embodiment, a situation where the optical characteristics to change are quantities of light will be taken as an example. In this case, when quantities of the light output from the optical fibers 41A to 41F are independently measured by using the light receiving elements 51A to 51F, the curvatures of the characteristic detection portions 42A to 42F are obtained.

Figure 2:
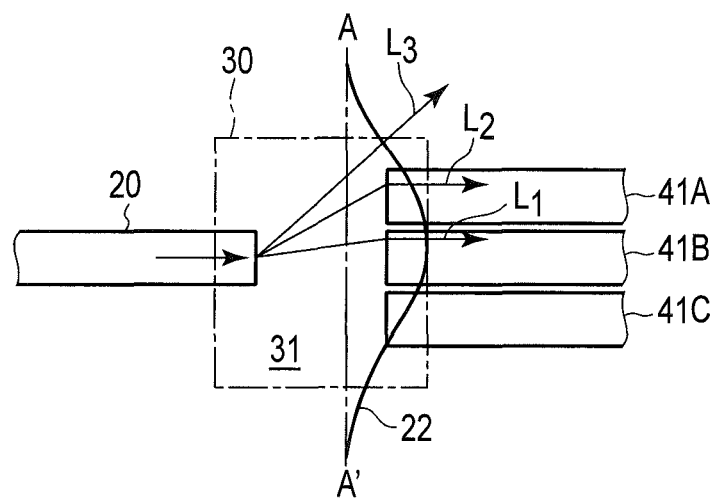
FIG. 2 schematically shows a structural example of a light distribution conversion unit of a light distribution unit shown in FIG. 1.

FIG. 2 schematically shows a structural example of the light distribution conversion unit 31 of the light distribution unit 30. In this example, the light distribution conversion unit 31 is constituted of a space between the optical fiber 2 and the optical fiber bundle 40. In other words, the light distribution conversion unit 31 is constituted of a gas, e.g., air that is present between the light exit end face of the optical fiber 20 and each light incidence end face of the optical fiber bundle 40.

FIG. 2 typically shows the three optical fibers 41A to 41C in the optical fiber bundle 40. The optical fiber 20 and the optical fibers 41A to 41C are arranged in such a manner that an optical axis of the optical fiber 20 on the light exit end face of the optical fiber 20 becomes parallel to optical axes of the optical fibers 41A to 41C on the light incidence end faces of the optical fibers 41A to 41C.

In FIG. 2, a curved line 22 indicates an intensity distribution on an A-A' cross section of a light beam exiting the optical fiber 20. The gas constituting the light distribution conversion unit 31 has a refractive index of 1 or more and functions to suppress spread of the light exiting the optical fiber 20. Therefore, the light exiting the optical fiber 20 can be efficiently distributed to the optical fibers 41A to 41C. Of light components $L_1$, $L_2$, and $L_3$ exiting the optical fiber 20, the light components $L_1$ and $L_2$ are distributed to the optical fibers 41B and 41A, but the light component $L_3$ turns to a loss without being distributed to all of the optical fibers 41A to 41C.

Figure 3:
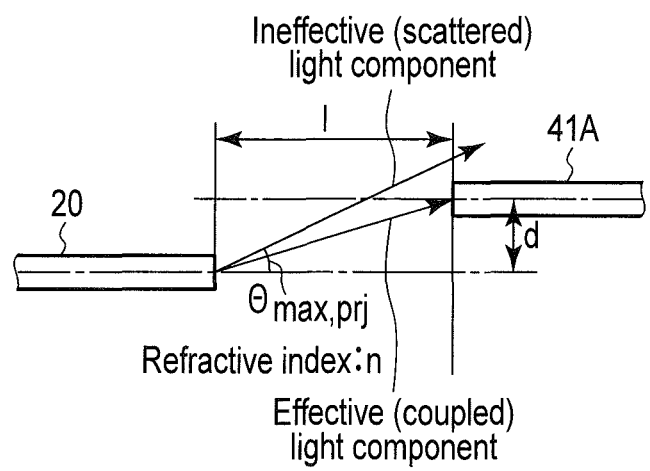
FIG. 3 shows a light supply optical fiber and a light detection optical fiber in the light distribution unit shown in FIG. 2.

Preferred conditions of the light distribution conversion unit 31 having the configuration shown in FIG. 2 will now be considered with reference to FIG. 3. FIG. 3 shows the optical fiber 20 and the optical fiber 41A in the optical fiber bundle 40. Here, the optical fiber 41A typically represents an optical fiber that is the farthest from the center of the optical fiber bundle 40.

As represented by the following Equation (1), a maximum exit angle $\theta_{max,\,prj}$ of light exiting the optical fiber 20 is restricted by a numerical aperture $NA_{prj}$ of the optical fiber 20 and a refractive index n of a transparent material that is present in front of the light exit end face of the optical fiber 20. Here, the exit angle of the light means an angle of the light in an exit direction relative to the optical axis of the optical fiber 20 on the light exit end face of the optical fiber 20.

$$\theta_{max,prj} = \text{Arcsin} \frac{NA_{prj}}{n} \quad (1)$$

Likewise, as represented by the following Equation (2), a maximum incidence angle $\theta_{max,\,det}$ of light that can enter the optical fiber 41A and travel through the optical fiber 41A is restricted by a numerical aperture $NA_{det}$ of the optical fiber 41A and a refractive index n of a transparent material that is present in front of the light incidence end face of the optical fiber 41A. Here, the incidence angle of the light means an angle of light in an incidence direction relative to the optical axis of the optical fiber 41A on the light incidence end face of the optical fiber 41A.

$$\theta_{max,det} = \text{Arcsin} \frac{NA_{det}}{n} \quad (2)$$

The light that enters the optical fiber 41A at an incidence angle larger than the maximum incidence angle $\theta_{max,\,det}$ cannot travel through the optical fiber 41A, namely, cannot be guided through the optical fiber 41A.

Based on a geometric relationship shown in FIG. 3, a condition required for the light exiting the optical fiber 20 to reach the optical fiber 41A through the transparent material having the refractive index n is represented by the following Equation (3).

$$\frac{d}{l} \leq \tan\theta_{max,prj} \quad (3)$$

Here, d is a distance from the center of the light exit end face of the optical fiber 20 to the center of the light incidence end face of the optical fiber 41A in a direction vertical to the optical axis of the optical fiber 20 on the light exit end face of the optical fiber 20, and l is a distance from the light exit end face of the optical fiber 20 to the light incidence end face of the optical fiber 41A in a direction parallel to the optical axis of the optical fiber 20 on the light exit end face of the optical fiber 20.

Further, a condition required for the light that has reached the optical fiber 41A to travel through the optical fiber 41A is represented by the following Equation (4).

$$\frac{d}{l} \leq \tan\theta_{max,det} \quad (4)$$

Therefore, to allow the light exiting the optical fiber 20 to reach the optical fiber 41A and allow the light that has reached the optical fiber 41A to travel through the optical fiber 41A, satisfying both Equation (3) and Equation (4) can suffice.

Figure 4:
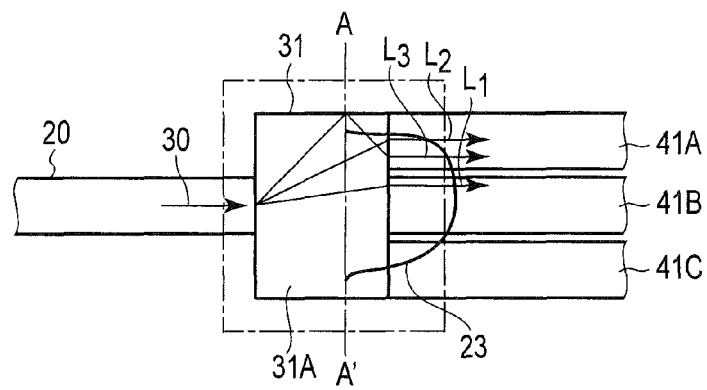
FIG. 4 schematically shows another structural example of the light distribution conversion unit of the light distribution unit shown in FIG. 1.

FIG. 4 schematically shows another structural example of the light distribution conversion unit 31 of the light distribution unit 30. In this example, the light distribution conversion unit 31 is constituted of a transparent member 31A having two opposed surfaces that are parallel to each other. The transparent member 31A is arranged in such a manner that the opposed surfaces become substantially vertical to the optical axis of the optical fiber 20 on the light exit end face of the optical fiber 20. The transparent member 31A has, e.g., a cylindrical shape. The light exit end face of the optical fiber 20 is arranged to face one of the opposed surfaces of the transparent member 31A, and the light incidence end face of the optical fiber 20 is arranged to face the other of the opposed surfaces of the transparent member 31A.

FIG. 4 typically shows the three optical fibers 41A to 41C in the optical fiber bundle 40 like FIG. 2. The optical fiber 20 and the optical fibers 41A to 41C are arranged in such a manner that the optical axis of the optical fiber 20 on the light exit end face of the optical fiber 20 becomes parallel to the optical axes of the optical fibers 41A to 41C on the light incidence end faces of the optical fibers 41A to 41C.

In FIG. 4, a curved line 23 indicates an intensity distribution of a light beam exiting the optical fiber 20 in an A-A' cross section. The transparent member 31A constituting the light distribution conversion unit 31 has a refractive index of 1 or more and functions to suppress spread of the light exiting the optical fiber 20. The transparent member 31A further has a function of reflecting light by a side surface thereof and serves to inwardly deflect light traveling toward the outside. Therefore, the light exiting the optical fiber 20 can be highly efficiently distributed to the optical fibers 41A to 41C. Light components $L_1$ and $L_2$ directly reach the optical fibers 41B and 41A to be distributed to the optical fibers 41B and 41A, respectively. Furthermore, a light component $L_3$ turns to a loss without being distributed to all of the optical fibers 41A to 41C in the configuration shown in FIG. 4, but it is reflected on the side surface of the transparent member 31A and distributed to, e.g., the optical fiber 41A in the configuration in FIG. 4.

Figure 5:
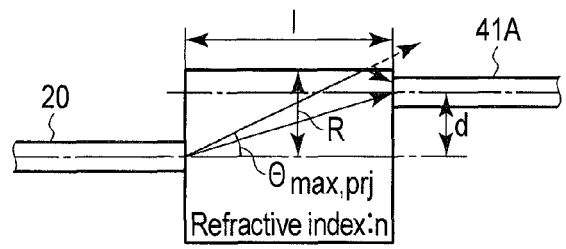
FIG. 5 shows a light supply optical fiber, a transparent member, and a light detection optical fiber in the light distribution unit shown in FIG. 4.

Preferred conditions of the light distribution conversion unit 31 in the configuration shown in FIG. 4 will now be considered with reference to FIG. 5. FIG. 5 shows the optical fiber 20, the transparent member 31A, and an optical fiber 41A in the optical fiber bundle 40. Here, the optical fiber 41A typically represents an optical fiber that is the farthest from the center of the optical fiber bundle 40 like FIG. 3.

The discussion on the configuration in FIG. 3 can be applied to the configuration in FIG. 5 as it is. Therefore, the maximum exit angle $\theta_{max,\,prj}$ of the light exiting the optical fiber 20 is represented by Equation (1) described above, and the maximum incidence angle $\theta_{max,\,det}$ of the light that can enter the optical fiber 41A and travel through the optical fiber 41A is represented by Equation (2) described above. Moreover, based on a geometric relationship in FIG. 5, a condition required for the light exiting the optical fiber 20 to directly reach the optical fiber 41A is represented by Equation (3) described above, and a condition required for the light that has reached the optical fiber 41A to travel through the optical fiber 41A is represented by Equation (4) described above.

In the configuration shown in FIG. 5, in regard to the light exiting the optical fiber 20, not only a component that directly reaches the optical fiber 41A but also a component reflected by the side surface of the transparent member 31A can be also distributed to the optical fiber 41A. Therefore, as to the condition required for the light exiting the optical fiber 20 to reach the optical fiber 41A, meeting the following Equation (5) in place of meeting Equation (3) can suffice.

$$\frac{R}{l} \leq \tan\theta_{max,prj} \quad (5)$$

The light distribution conversion unit 31 may have a function of adjusting light distribution so that the light exiting the optical fiber 20 can be coupled to the optical fiber bundle 40. Therefore, the light distribution conversion unit 31 may have a function of suppressing spread of light. Here, although the example where the light distribution conversion unit 31 is constituted of the cylindrical transparent member 31A, i.e., a transparent cylindrical rod having the refractive index of 1 or more has been described, the light distribution conversion unit 31 may be also constituted of a transparent conical rod having a refractive index of 1 or more, a lens (including a refractive index distribution lens on a rod or the like), a diffraction grating or a hologram that controls the light distribution, or the like. Additionally, to prevent light reflected on a side surface of the cylindrical rod or the conical rod from passing through the side surface and being scattered to the outside, forming a reflection film on the side surface of the cylindrical rod or the conical rod is desirable. Further, to obtain an effect that is similar to this, it is desirable to set a refractive index or a shape of the rod so that all light rays defined by NA of the supply optical fiber undergo the total reflection.

According to the optical sensor of this embodiment, the light exiting the optical fiber 20 can be preferably distributed to the optical fibers 41A to 41F.

Various changes or modifications can be applied to this embodiment.

In the above description, the example where the characteristic detection portions 42A to 42F are provided at positions different from each other along the longitudinal direction of the optical fibers 41A to 41F, respectively is given, but each pair of the characteristic detection portions 42A to 42F may be provided at positions that are the same along the longitudinal direction of the optical fibers 41A to 41F but different from each other 90 degrees around the central axes of the optical fibers 41A to 41F.

Although the example where bent states of the characteristic detection portions 42A to 42F are detected based on the light guide loss of the optical fibers 41A to 41F has been described, they may be detected based on other characteristics, e.g., a light wavelength or an optical phase.

Although the example where the characteristic detection portions 42A to 42F have the curvature detecting function has been described, the characteristic detection portions 42A to 42F may have other detecting functions. For example, the characteristic detection portions 42A to 42F may have a function of detecting stress, a temperature, an electric field, a magnetic field, or heat. That is, optical characteristics of the characteristic detection portions 42A to 42F may vary depending on stress states or temperatures of the characteristic detection portions 42A to 42F or an electric field, a magnetic field, or heat that functions with respect to the characteristic detection portions 42A to 42F without being restricted to bent shapes of the characteristic detection portions 42A to 42F. Besides, the characteristic detection portions 42A to 42F may have a function of detecting chemical substances. That is, optical characteristics of the characteristic detection portions 42A to 42F may vary depending on the chemical substances that are in contact with the characteristic detection portions 42A to 42F.

Although the example where the light source 10 and the light separating detector 50 are arranged on the same side as the light distribution unit 30 has been described, the light source 10 and the light separating detector 50 may be arranged on the opposite side of the light distribution unit 30.

Second Embodiment

Figure 6:
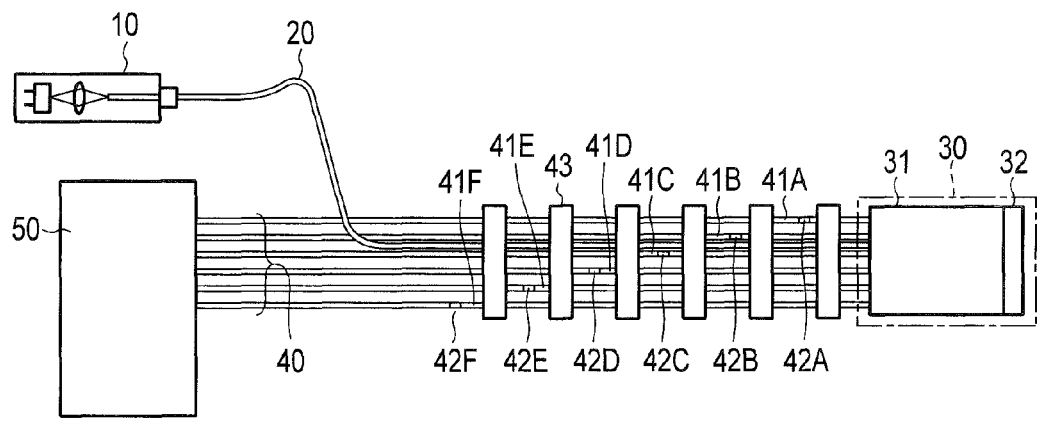
FIG. 6 shows an entire configuration of an optical sensor according to a second embodiment.

A second embodiment according to the present invention will now be described hereinafter in detail with reference to the drawings. It is to be noted that the present invention is not limited by this embodiment. FIG. 6 shows an entire configuration of an optical sensor according to this embodiment. In FIG. 6, members denoted by reference numerals equal to those of the members shown in FIG. 1 are like members, and a detailed description thereof will be omitted. Differences will be mainly explained hereinafter. That is, parts that will not be described below are the same as those in the first embodiment.

As shown in FIG. 6, the optical sensor includes a light source 10, an optical fiber 20 optically coupled to the light source 10, an optical fiber bundle 40, a light distribution unit 30 that distributes light from the optical fiber 20 to the optical fiber bundle 40, and a light separating detector 50 that separates and detects light guided through the optical fiber bundle 40.

The optical fiber bundle 40 includes optical fibers 41A, 41B, 41C, 41D, 41E, and 41F. The optical fibers 41A to 41F are bundled by tying bands 43 at positions provided at intervals in the longitudinal direction. As shown in FIG. 7, the optical fibers 41A to 41F are equally arranged around the optical fiber 20.

The light distribution unit 30 includes a light distribution conversion unit 31 to convert light distribution characteristics of the light exiting the optical fiber 20 and couple the light to the optical fibers 41A to 41F. The light distribution conversion unit 31 has a transparent material having a refractive index of 1 or more. This transparent material has the refractive index of 1 or more and functions to suppress spread of the light exiting the optical fiber 20.

The light distribution unit 30 further includes a light turnback unit 32 to turn back a light traveling direction. A light exit end face of the optical fiber 20 and light incidence end faces of the optical fibers 41A to 41F are arranged to face the light turnback unit 32 through the light distribution conversion unit 31. Light exiting the optical fiber 20 is optically coupled to the optical fibers 41A to 41F through the light distribution conversion unit 31 and the light turnback unit 32.

Light generated by the light source 10 is guided through the optical fiber 20. The light exiting the light exit end face of the optical fiber 20 travels through the light distribution conversion unit 31 and reaches the light turnback unit 32, a traveling direction of the light is turned back by the light turnback unit 32, and this light again travels through the light distribution conversion unit 31 and is distributed to the optical fibers 41A to 41F. Spread of the light exiting the light exit end face of the optical fiber 20 is suppressed by the light distribution conversion unit 31 until it reaches the optical fibers 41A to 41F. The light distributed to the optical fibers 41A to 41F are guided to the light separating detector 50 through the optical fibers 41A to 41F. This light separating detector 50 separates and detects the light guided through the optical fibers 41A to 41F.

When the characteristic detection portions 42A to 42F are bent due to curvatures of the optical fibers 41A to 41F, optical characteristics vary in dependence upon magnitudes and directions of the curvatures, and hence quantities of light output from the optical fibers 41A to 41F change. When the quantities of light output from the optical fibers 41A to 41F are independently measured by the light separating detector 50, the curvatures of the characteristic detection portions 42A to 42F are obtained.

FIG. 8 schematically shows a structural example of the light distribution conversion unit 31 of the light distribution unit 30. In this example, the light distribution conversion unit 31 is constituted of a space that extends from the optical fiber 20 to the optical fiber bundle 40 via the light turnback unit 32. In other words, the light distribution conversion unit 31 is constituted of a gas, e.g., air that is present between both the end faces, i.e., the light exit end face of the optical fiber 20 and the light incidence end faces of the optical fiber bundle 40 and the light turnback unit 32.

FIG. 8 typically shows the two optical fibers 41A and 41D in the optical fiber bundle 40. The optical fiber 20 and the optical fibers 41A and 41D are arranged in such a manner that an optical axis of the optical fiber 20 on the light exit end face of the optical fiber 20 becomes parallel to optical axes of the optical fibers 41A to 41D on the light incidence end faces of the optical fibers 41A to 41D.

In FIG. 8, a curved line 24 indicates an intensity distribution of a light beam exiting the optical fiber 20 on a B-B' cross section. The gas constituting the light distribution conversion unit 31 has a refractive index of 1 or more and functions to suppress spread of the light exiting the optical fiber 20. Therefore, the light exiting the optical fiber 20 can be efficiently distributed to the optical fibers 41A and 41D. Of light components $L_1$, $L_2$, and $L_3$ exiting the optical fiber 20, both the light components $L_1$ and $L_2$ are distributed to the optical fiber 41A, but the light component $L_3$ turns to a loss without being distributed to both the optical fibers 41A and 41D.

Preferred conditions of the light distribution conversion unit 31 having the configuration shown in FIG. 8 will now be considered with reference to FIG. 9. FIG. 9 shows the optical fiber 20 and the optical fiber 41A in the optical fiber bundle 40. Here, the optical fiber 41A typically represents an optical fiber that is the farthest from the center of the optical fiber bundle 40.

As represented by Equation (1) described above, a maximum exit angle $\theta_{max,prj}$ of light exiting the optical fiber 20 is restricted by a numerical aperture $NA_{prj}$ of the optical fiber 20 and a refractive index n of a transparent material that is present in front of the light exit end face of the optical fiber 41A.

$$\theta_{max,prj} = \text{Arcsin} \frac{NA_{prj}}{n} \quad (1)$$

Likewise, as represented by Equation (2) described above, a maximum incidence angle $\theta_{max,det}$ of light that can enter the optical fiber 41A and travel through the optical fiber 41A is restricted by a numerical aperture $NA_{det}$ of the optical fiber 41A and a refractive index n of a transparent material that is present in front of the light incidence end face of the optical fiber 41A.

$$\theta_{max,det} = \text{Arcsin} \frac{NA_{det}}{n} \quad (2)$$

Based on a geometric relationship shown in FIG. 9, a condition required for the light exiting the optical fiber 20 to reach the optical fiber 41A through the transparent material having the refractive index n is represented by the following Equation (6).

$$\frac{d}{l_1 + l_2} \leq \tan\theta_{max,prj} \quad (6)$$

Here, d is a distance from the center of the light exit end face of the optical fiber 20 to the center of the light incidence end face of the optical fiber 41A in a direction vertical to the optical axis of the optical fiber 20 on the light exit end face of the optical fiber 20, $l_1$ is a distance from the light exit end face of the optical fiber 20 to the light turnback unit 32 in a direction parallel to the optical axis of the optical fiber 20 on the light exit end face of the optical fiber 20, and $l_2$ is a distance from the light turnback unit 32 to the light incidence end face of the optical fiber 41A in a direction parallel to the optical axis of the optical fiber 41A on the light incidence end face of the optical fiber 41A.

Further, a condition required for the light that has reached the optical fiber 41A to travel through the optical fiber 41A is represented by the following Equation (7).

$$\frac{d}{l_1 + l_2} \leq \tan\theta_{max,det} \quad (7)$$

Therefore, to allow the light exiting the optical fiber 20 to reach the optical fiber 41A via the light turnback unit 32 and allow the light that has reached the optical fiber 41A to travel through the optical fiber 41A, satisfying both Equation (6) and Equation (7) can suffice.

FIG. 10 schematically shows another structural example of the light distribution conversion unit 31 of the light distribution unit 30. In this example, the light distribution conversion unit 31 is constituted of a transparent member 31A having two opposed surfaces that are parallel to each other. The transparent member 31A is arranged in such a manner that the opposed surfaces become substantially vertical to the optical axis of the optical fiber 20 on the light exit end face of the optical fiber 20. The transparent member 31A has, e.g., a cylindrical shape. The light exit end face of the optical fiber 20 and the light incidence end faces of the optical fibers 41A and 41B are arranged to face one of the opposed surfaces of the transparent member 31A, and the light turnback unit 32 is arranged to face the other of the opposed surfaces of the transparent member 31A. For example, the light turnback unit 32 may be constituted of a member that is different from the transparent member 31A and arranged in contact with a flat surface of the transparent member 31A. In another example, the light turnback unit 32 may be formed on the flat surface of the transparent member 31A and constituted of a member that is integral with the transparent member 31A.

FIG. 10 typically shows the two optical fibers 41A and 41D in the optical fiber bundle 40 like FIG. 8. The optical fiber 20 and the optical fibers 41A and 41D are arranged in such a manner that the optical axis of the optical fiber 20 on the light exit end face of the optical fiber 20 becomes parallel to the optical axes of the optical fibers 41A and 41D on the light incidence end faces of the optical fibers 41A and 41D.

In FIG. 10, a curved line 25 indicates an intensity distribution of a light beam exiting the optical fiber 20 in a B-B' cross section. The transparent member 31A constituting the light distribution conversion unit 31 has a refractive index of 1 or more and functions to suppress spread of the light exiting the optical fiber 20. The transparent member 31A further has a function of reflecting light on a side surface thereof and serves to inwardly deflect light traveling toward the outside. Therefore, the light exiting the optical fiber 20 can be highly efficiently distributed to the optical fibers 41A and 41D. Light components $L_1$ and $L_2$ reach the optical fiber 41A to be distributed to the optical fiber 41A, respectively. Furthermore, a light component $L_3$ turns to a loss without being distributed to both the optical fibers 41A and 41D in the configuration shown in FIG. 8, but it is reflected on the side surface of the transparent member 31A and distributed to, e.g., the optical fiber 41A in the configuration in FIG. 10.

Preferred conditions of the light distribution conversion unit 31 in the configuration shown in FIG. 10 will now be considered with reference to FIG. 11. FIG. 11 shows the optical fiber 20, the transparent member 31A, and the optical fiber 41A in the optical fiber bundle 40. Here, the optical fiber 41A typically represents an optical fiber that is the farthest from the center of the optical fiber bundle 40 like FIG. 9.

The discussion on the configuration in FIG. 9 can be applied to the configuration in FIG. 5 as it is. The maximum exit angle $\theta_{max,\,prj}$ of the light exiting the optical fiber 20 is represented by Equation (1) described above, and the maximum incidence angle $\theta_{max,\,det}$ of the light that can enter the optical fiber 41A and travel through the optical fiber 41A is represented by Equation (2) described above. Moreover, based on a geometric relationship in FIG. 11, a condition required for the light exiting the optical fiber 20 to reach the optical fiber 41A through the light turnback unit 32 is represented by Equation (6) described above, and a condition required for the light that has reached the optical fiber 41A to travel through the optical fiber 41A is represented by Equation (7) described above.

In the configuration shown in FIG. 11, in regard to the light exiting the optical fiber 20, not only a component that directly reaches the optical fiber 41A after traveling through the light turnback unit 32 but also a component reflected by the side surface of the transparent member 31A can be also distributed to the optical fiber 41A. Therefore, as to the condition required for the light exiting the optical fiber 20 to reach the optical fiber 41A, meeting the following Equation (8) in place of meeting Equation (6) described above can suffice.

$$\frac{R}{l_1 + l_2} \leq \tan\theta_{max,prj} \quad (8)$$

According to the optical sensor of this embodiment, the light exiting the optical fiber 20 can be preferably distributed to the optical fibers 41A to 41F.

The light turnback unit 32 of the light distribution unit 30 can be constituted of each of various optical elements. For example, as shown in FIG. 12, the light turnback unit 32 may be constituted of a mirror 32A. As another structural example, as shown in FIG. 13, the light turnback unit 32 may be constituted of a reflection type refraction grating 32B. Furthermore, the reflection type refraction grating 32B may have a function of adjusting the light distribution of the light exiting the optical fiber 20. In this structural example, the transparent member 31A as well as the reflection type refraction grating 32B can adjust the light distribution of the light exiting the optical fiber 20, and hence the light exiting the optical fiber 20 can be further efficiently distributed to the optical fibers 41A and 41D. Moreover, as still another structural example, the light turnback unit 32 may be constituted of a scattering member or may be constituted of a flat surface itself on the opposite side of the flat surface of the transparent member 31A that faces the end faces of the optical fiber 20 or the optical fibers 41A and 41D.

Various changes or modifications can be applied to this embodiment. For example, the changes or the modifications described in the first embodiment may be applied as they are.

Besides, for example, as shown in FIG. 14, the light distribution unit 30 may have a configuration that the optical fiber 20 is optically coupled to the center of the transparent member 31B constituting the light distribution conversion unit 31. In this structural example, the optical fibers 20, 41A, and 41D have cores 20a, 41Aa, and 41Da and clads 20b, 41Ab, and 41Db, respectively, and the core 20a of the optical fiber 20 extends in the transparent member 31B over the full length. The light guided through the optical fiber 20 outgoes through the transparent member 31B from a side surface of the core 20A placed in the transparent member 31B and is distributed to the optical fibers 41A and 41D via the light turnback unit 32.

Further, as shown in FIG. 15, the light distribution unit 30 may have a configuration that the optical fiber 20 is optically coupled to the center of the transparent member 31C constituting the light distribution conversion unit 31 and the optical fibers 41A and 41D are optically coupled to the side surface of the transparent member 31C. In this structural example, the optical fibers 20, 41A, and 41D have cores 20a, 41Aa, and 41Da and clads 20b, 41Ab, and 41Db, respectively, and the core 20a of the optical fiber 20 extends to the inside of the transparent member 31C and is terminated in the transparent member 31C. Side surfaces of the cores 41Aa and 41Da of the optical fibers 41A and 41D are in contact with the side surface of the transparent member 31C, whereby the optical fibers 41A and 41D are optically coupled to the side surface of the transparent member 31C. The light guided through the optical fiber 20 outgoes through the transparent member 31C from an end face or a side surface of the core 20a placed in the transparent member 31C and is coupled to the cores 41Aa and 41Da of the optical fibers 41A and 41D via the side surface of the transparent member 31C through the light turnback unit 32.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical sensor comprising:
   a light source;
   alight supply light guide member optically coupled to the light source;
   detection light guide members each of which includes a characteristic detection portion whose optical characteristics vary in accordance with a physicochemical state;
   a light distribution unit to distribute light from the light supply light guide member to the detection light guide members; and
   a light separating detector to separate and detect the light guided by the detection light guide members.

2. The optical sensor according to claim 1, wherein the light distribution unit includes a light distribution conversion unit to convert light distribution characteristics of the light exiting the light supply light guide member and couple the light to the detection light guide members.

3. The optical sensor according to claim 2, wherein the light distribution conversion unit has a transparent material having a refractive index of 1 or more, and a maximum exit angle $\theta_{max,prj}$ of the light exiting the light supply light guide member, a numerical aperture $NA_{prj}$ of the light supply light guide member, a refractive index n of the transparent material, a distance l from a light exit end face of the light supply light guide member to light incidence end faces of the detection light guide members in a direction parallel to an optical axis of the light supply light guide member on the light exit end face of the light supply light guide member, and a distance d from the center of the light exit end face of the light supply light guide member to the center of the light incidence end faces of the detection light guide members in a direction vertical to the optical axis of the light supply light guide member on the light exit end face of the light supply light guide member meet the following equation:

$$\theta_{max,prj} = \text{Arcsin}\frac{NA_{prj}}{n},$$

$$\frac{d}{l} \leq \tan\theta_{max,prj}.$$

4. The optical sensor according to claim 3, wherein a maximum incidence angle $\theta_{max,det}$ of the light that is able to travel through the detection light guide members and a numeral aperture $NA_{det}$ of each of the detection light guide members meet the following equation:

$$\theta_{max,det} = \text{Arcsin}\frac{NA_{det}}{n},$$

$$\frac{d}{l} \leq \tan\theta_{max,det}.$$

5. The optical sensor according to claim 4, wherein the light distribution unit further includes a light turnback unit to turn back a traveling direction of the light, the light exit end face of the light supply light guide member and the light incidence end faces of the detection light guide members are arranged to face the light turnback unit through the light distribution conversion unit, and the light exiting the light supply light guide member is optically coupled to the detection light guide members through the light distribution conversion unit and the light turnback unit.

6. The optical sensor according to claim 5, wherein the transparent material is constituted of a transparent member having two opposed surfaces that are substantially vertical to the optical axis of the light supply light guide member on the light exit end face of the light supply light guide member.

7. The optical sensor according to claim 5, wherein the light turnback unit is constituted of one of a flat surface of the transparent member, a mirror, a diffraction grating, and a scattering member.

8. The optical sensor according to claim 5, wherein both the light exit end face of the light supply light guide member and the light incidence end faces of the detection light guide members are arranged to face a flat surface of the transparent member.

9. The optical sensor according to claim 8, wherein the transparent member has a cylindrical shape, and a radius R of the transparent member meets the following equation:

$$\frac{R}{l} \leq \tan\theta_{max,prj}.$$

10. The optical sensor according to claim 9, wherein a reflection film is formed on a side surface of the transparent member.

11. The optical sensor according to claim 9, wherein a refractive index and a shape of the transparent member are set so that all light rays defined by the numerical aperture of the light supply light guide member undergo the total reflection.

12. The optical sensor according to claim 2, wherein the light supply light guide member is optically coupled to the center of the transparent member, the detection light guide members are optically coupled to the side surface of the transparent member, and the light exiting the light supply light guide member is coupled to the detection light guide members through the side surface of the transparent member.

13. The optical sensor according to claim 2, wherein the light exit end face of the light supply light guide member and the light incidence end faces of the detection light guide members are arranged to face each other through the light distribution conversion unit, and the light exiting the light supply light guide member is optically coupled to the detection light guide members through the light distribution conversion unit.

14. The optical sensor according to claim 13, wherein the light distribution conversion unit has a transparent material having a refractive index of 1 or more, and
a maximum exit angle $\theta_{max,prj}$ of the light exiting the light supply light guide member, a numerical aperture $NA_{prj}$ of the light supply light guide member, a refractive index n of the transparent material, a distance l from a light exit end face of the light supply light guide member to light incidence end faces of the detection light guide members in a direction parallel to an optical axis of the light supply light guide member on the light exit end face of the light supply light guide member, and a distance d from the center of the light exit end face of the light supply light guide member to the center of the light incidence end faces of the detection light guide members in a direction vertical to the optical axis of the light supply light guide member on the light exit end face of the light supply light guide member meet the following equation:

$$\theta_{max,prj} = \text{Arcsin}\frac{NA_{prj}}{n},$$

$$\frac{d}{l} \leq \tan\theta_{max,prj}.$$

15. The optical sensor according to claim 13, wherein a maximum incidence angle $\theta_{max,det}$ of the light that is able to travel through the detection light guide members and a numeral aperture $NA_{det}$ of each of the detection light guide members meet the following equation:

$$\theta_{max,det} = \text{Arcsin}\frac{NA_{det}}{n},$$

$$\frac{d}{l} \leq \tan\theta_{max,det}.$$

16. The optical sensor according to claim 15, wherein the transparent material is constituted of a transparent member having two opposed surfaces that are substantially vertical to the optical axis of the light supply light guide member on the light exit end face of the light supply light guide member.

17. The optical sensor according to claim 16, wherein the light exit end face of the light supply light guide member is arranged to face one opposed surface of the transparent member, and the light incidence end face of the detection light guide member is arranged to face the other opposed surface of the transparent member.

18. The optical sensor according to claim 17, wherein the transparent member has a cylindrical shape, and a radius R of the transparent member meets the following equation:

$$\frac{R}{l} \leq \tan\theta_{max,prj}.$$

19. The optical sensor according to claim 18, wherein a reflection film is formed on a side surface of the transparent member.

20. The optical sensor according to claim 18, wherein a refractive index and a shape of the transparent member are set so that all light rays defined by the numerical aperture of the light supply light guide member undergo the total reflection.

21. The optical sensor according to claim 13, wherein the light supply light guide member is optically coupled to the center of the transparent member, the detection light guide members are optically coupled to the side surface of the transparent member, and the light exiting the light supply light guide member is coupled to the detection light guide members through the side surface of the transparent member.

22. The optical sensor according to claim 2, wherein the characteristic detection portion is formed on each detection light guide member on an optical path extending from the light distribution unit to the light separating detector.

23. The optical sensor according to claim 2, wherein the optical characteristics of the characteristic detection portion vary in dependence upon one of a bent shape, a stress state, and a temperature of the characteristic detection portion, an electric field, a magnetic field, and heat that act on the characteristic detection portion.

24. The optical sensor according to claim 2, wherein the optical characteristics of the characteristic detection portion vary in dependence upon a chemical substance that is in contact with the characteristic detection portion.

* * * * *